US00PP13559P3

(12) United States Plant Patent
Turner

(10) Patent No.: US PP13,559 P3
(45) Date of Patent: Feb. 11, 2003

(54) BRACTEANTHA PLANT NAMED 'ANTIQUE SHADES'

(75) Inventor: Matthew Turner, Penrith South (AU)

(73) Assignee: Oasis Horticulture Pty. Ltd. (AU)

( * ) Notice: Subject to any disclaimer, the term of this patent is extended or adjusted under 35 U.S.C. 154(b) by 0 days.

(21) Appl. No.: 09/819,272

(22) Filed: Mar. 28, 2001

(65) Prior Publication Data

US 2002/0174472 P1 Nov. 21, 2002

(51) Int. Cl.[7] ..... A01H 5/00

(52) U.S. Cl. ..... Plt./359

(58) Field of Search ..... Plt./359

*Primary Examiner*—Bruce R. Campell
*Assistant Examiner*—June Hwu
(74) *Attorney, Agent, or Firm*—Wood, Phillips, Katz, Clark & Mortimer

(57) ABSTRACT

A new and distinct Bracteantha plant named 'Antique Shades', characterized by its pale purple flowers, upright growth habit, and medium green leaves.

1 Drawing Sheet

LATIN NAME OF THE GENUS AND SPECIES OF PLANT CLAIMED

*Bracteantha bracteata.*

VARIETY DEMONINATIION

'Antique Shades'.

BACKGROUND OF THE INVENTION

The present invention comprises a new and distinct Bracteantha plant, botanically known as *Bracteantha bracteata* and hereinafter referred to by the cultivar name 'Antique Shades' characterized by its pale purple flowers.

The new cultivar was developed by the inventor through a controlled breeding program at New South Wales, Australia.

The female (seed) parent of 'Antique Shades' was the cultivar 'Spectrum' (not patented in the United States), characterized by its medium tall plant height and red-purple bract color. The male (pollen) parent of 'Antique Shades' was the cultivar 'Diamond Head' (not patented in the United States), characterized by its yellow bract color. 'Antique Shades' was selected as one of the flowering progeny of the above cross.

Asexual reproduction of the new cultivar has been carried out in Arroyo Grande, Calif. and West Chicago, Ill. Such asexual reproduction, by terminal cuttings, has demonstrated that the characteristics of the new cultivar as herein described are firmly fixed and retained through successive generations of such asexual propagation.

SUMMARY OF THE INVENTION

It was found that the cultivar of the present invention:

(a) exhibits pale purple flowers, (b) forms medium green foliage, (c) exhibits a good basal branching character, and (d) exhibits an upright growth habit.

When the new cultivar of the present invention is compared to Florabella 'Pink', it is found that the new cultivar is more compact, exhibits different pubescence on stems and leaves and has flowers of a darker purple color as detailed in TABLE 1, below.

TABLE 1

| CHARACTERISTIC | 'ANTIQUE SHADES' | FLORABELLA 'PINK' |
|---|---|---|
| PLANT HEIGHT-cm | 18 | 23 |
| PLANT DIAMETER-cm | 30 | 22 |
| # LATERAL BRANCHES | 9 | 10 |
| INTERNODE LENGTH-cm | 4 mm | 1.5 cm |
| STEM TEXTURE | HIRSUTE | TOMENTOSE |
| LEAF LENGTH-cm | 7.2 | 8 |
| PENDUNCLE LENGTH-cm | 6 | 7.5 |
| PENDUNCLE TEXTURE | PUBERULENT | TOMENTOSE |
| INFLORESCENCE DIAMETER-CM | 3.7 | 4.2 |

BRIEF DESCRIPTION OF PHOTOGRAPH

The accompanying photograph show as nearly true as it is reasonably possible to make the same in color illustrations of this type, typical flower and foliage characteristics of the new cultivar. The plants were grown for 12 weeks in a greenhouse at West Chicago, Ill., U.S.A.

DETAILED BOTANICAL DESCRIPTION

The 'Antique Shades' cultivar has not been observed under all possible environmental conditions to date. Accordingly, it is possible that the phenotype may vary somewhat with variations in the environment, such as temperature, light intensity, and day length.

The chart used in the identification of colors described herein is The R.H.S. Colour Chart of The Royal Horticultural Society, London, England. The color values were determined on Feb. 15, 2001. The readings were taken between 10:00 and 11:00 a.m. under natural daylight conditions. The plants were produced from cuttings taken from stock plants and grown in a double polycarbonate covered greenhouse under conditions comparable to those used in commercial practice while utilizing a soilless growth medium and maintaining temperatures of approximately 72° F. during the day and approximately 65° F. during the night.

Classification:

*Botanical.*—*Bracteantha bracteata* cultivar 'Antique Shades'.

*Commercial.* —Helichrysum.

Parentage:

*Female parent.*—'Spectrum'.

*Male parent.*—'Diamond Head'.

Propagation:

*Type cutting.*—Terminal tip.

*Time to initiate roots.*—Approximately 30 to 50 days with the shorter times generally being experienced in the summer and the longer times in the winter.

Plant description:

*Habit of growth.*—Moderate. A mature plant, 14 weeks after the planting of a rooted cutting, commonly measures approximately 18 cm in height and approximately 30 cm in diameter.

*Branching habit.*—Freely basal branching although pinching improves basal branching. Commonly develops approximately 9 lateral branches.

*Form.*—Upright, mounded.

*Lateral stem.*—Diameter: Approximately 4 mm with hirsute pubescence. Color: 145B. Internode length: Approximately 4 mm.

*Foliage.*—Arrangement: Alternate. Shape: Lanceolate with entire margin, broadly acute apex and clasping base. Size: Approximately 7.2 cm in length and approximately 9 mm at widest point. Upper surface is rough and 137A. Lower surface is smooth 137C. Venation of both surfaces: Closest to 145C.

Flowering description:

*Flowering habit.*—Freely flowering.

*Natural flowering season.*—Spring through fall.

*Inflorescence type.*—Single, composite, persistent.

*Flowers arrangement.*—Acropetally on a capitulum.

*Bud.*—Size: 2 cm in length, 2 cm in diameter. Color: Closest to 71A.

*Inflorescence diameter.*—Approximately 3.7 cm.

*Involucral bracts.*—Quantity: Approximately 11 whorls. Aspect: Appear flat at maturity then become downwardly pointing with age. Appearance: Smooth, papery. Shape: Linear. Size: Length — 1.1 cm, width varies from 1 to 4 mm. Color — Upper surface, of fully opened inner whorls of bracts is between 12C and 12D. The lower surface of inner whorls of bracts is between 12C and 12D with specks of 59C. The upper surface of fully opened outer whorls of bracts is between 12C and 12D with tips of 59B. The lower surface of fully opened outer whorls of bracts if between 12C and 12D with tips of 67C. The outer phyllaries are closest to 161D.

*Capitulum diameter.*—1.2 cm.

*Disc florets.*—Quantity: Numerous. Shape: Tubular. Length: Approximately 6 mm. Color: Immature disc florets are 21C; mature disc florets are 21A.

*Peduncle.*—Length: Approximately 6 cm. Strength: good. Aspect: Erect. Color: 144C. Texture: Puberulent.

*Fragrance.*—None.

*Lastingness of flowers.*—The flowers of the new cultivar are not used as fresh cut flowers. They would be expected to last indefinitely as dries flowers but may fall apart after six to twelve months.

*Reproductive organs.*—Stigma color 25A. Style length is 3 mm and color is 3C. There are two anthers per disc floret. Anthers are 17B and 2 mm in length. Pollen color: 21A.

*Seed development.*—Seed production has not been observed.

*Disease resistance.*—Resistance to pathogens common to Bracteantha has not been observed.

I claim:

1. A new and distinct cultivar of Bracteantha plant named 'Antique Shades' substantially as herein shown and described, which:

(a) exhibits pale purple flowers, (b) forms medium green foliage, (c) exhibits a good basal branching character, and (d) exhibits an upright growth habit.

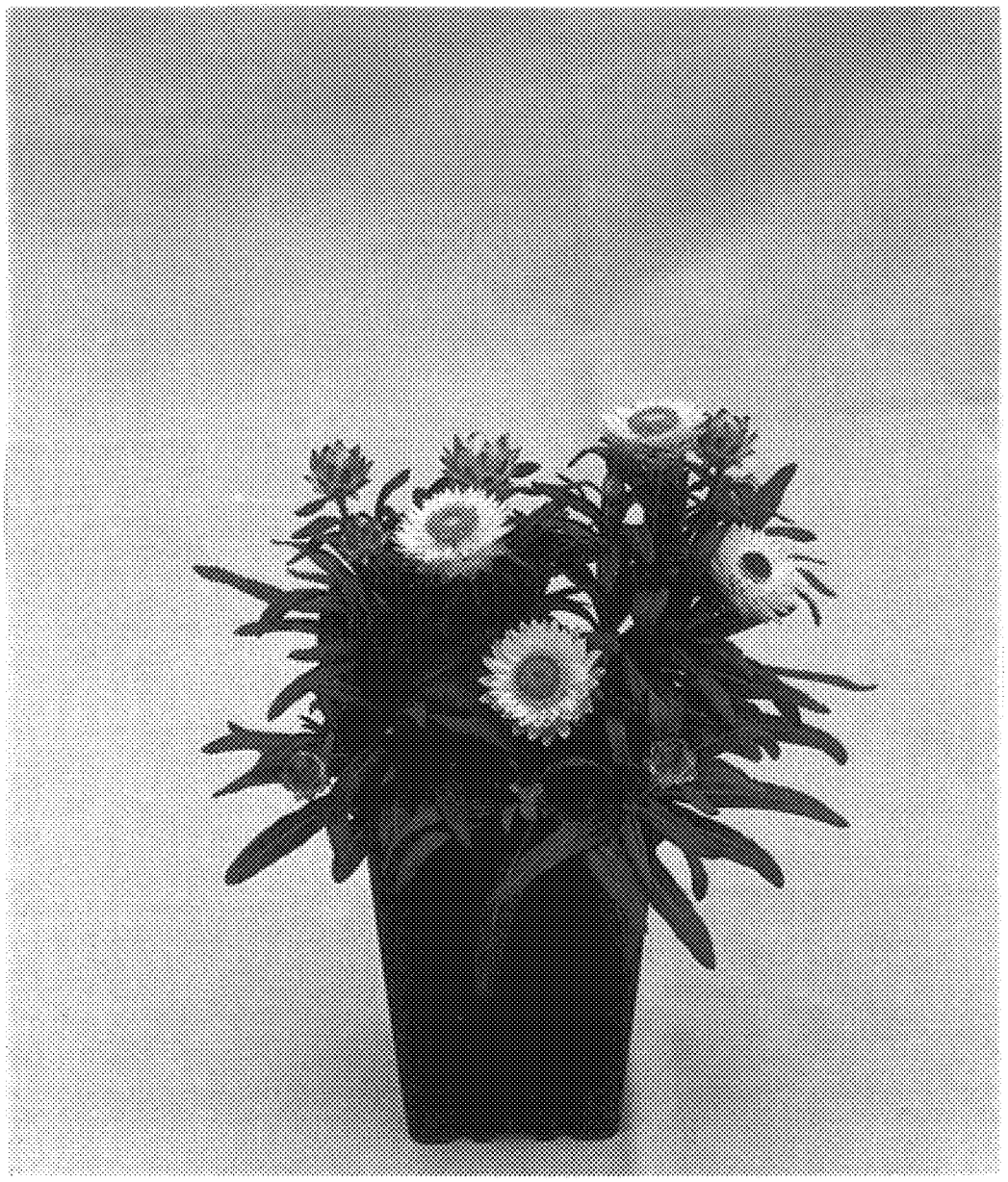

* * * * *